US00PP32340P2

(12) United States Plant Patent
Heuger

(10) Patent No.: US PP32,340 P2
(45) Date of Patent: Oct. 13, 2020

(54) ***HELLEBORUS* PLANT NAMED 'COSEH 5900'**

(50) Latin Name: ***Helleborus niger* X *Helleborus* x *hybridus***
Varietal Denomination: COSEH 5900

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,735

(22) Filed: Nov. 29, 2019

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Helleborus* plant named 'COSEH 5900', characterized by its upright and mounded plant habit; vigorous growth habit; dark green-colored leaves; freely flowering habit; single white-colored flowers; and good garden performance.

2 Drawing Sheets

Figure 1:
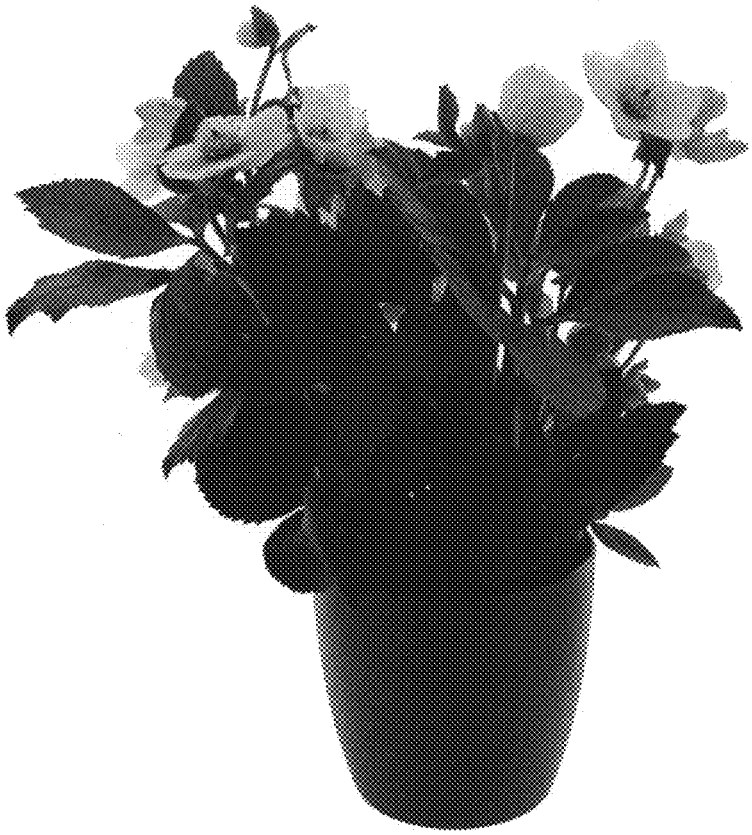

Botanical designation: *Helleborus niger* X *Helleborus* x *hybridus*.

Cultivar denomination: 'COSEH 5900'.

CROSS-REFERENCED TO CLOSELY-RELATED APPLICATIONS

Title: *Helleborus* Plant Named 'COSEH 5600'
Applicant: Josef Heuger
Filed: Concurrently with the instant application U.S. Plant patent application Ser. No. 16/602,791
Title: *Helleborus* Plant Named 'COSEH 5700'
Applicant: Josef Heuger
Filed: Concurrently with the instant application U.S. Plant patent application Ser. No. 16/602,738
Title: *Helleborus* Plant Named 'COSEH 6900'
Applicant: Josef Heuger
Filed: Concurrently with the instant application U.S. Plant patent application Ser. No. 16/602,736
Title: *Helleborus* Plant Named 'COSEH 7100'
Applicant: Josef Heuger
Filed: Concurrently with the instant application U.S. Plant patent application Ser. No. 16/602,734
Title: *Helleborus* Plant Named 'COSEH 7500'
Applicant: Josef Heuger
Filed: Concurrently with the instant application U.S. Plant patent application Ser. No. 16/602,737

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 5900'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2011 of a unnamed selection of *Helleborus niger*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in October, 2013.

Asexual reproduction of the new *Helleborus* plant by divisions in a controlled environment in Glandorf, Germany since February, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5900'. These characteristics in combination distinguish 'COSEH 5900' as a new and distinct *Helleborus* plant:

1. Upright and mounded plant habit.
2. Vigorous growth habit.
3. Dark green-colored leaves.
4. Freely flowering habit.
5. Single white-colored flowers.
6. Good garden performance.

Plants of the new *Helleborus* differ from plants of the female parent selection in the following characteristics:

1. Plants of the new *Helleborus* have thicker peduncles than plants of the female parent selection.
2. Plants of the new *Helleborus* have smaller flowers than plants of the female parent selection.

Plants of the new *Helleborus* differ from plants of the male parent selection in the following characteristics:

1. Plants of the new *Helleborus* have larger flowers than plants of the male parent selection.
2. Flower of plants of the new *Helleborus* are white in color whereas flowers of plants of the male parent selection are yellowish white in color.

Plants of the new *Helleborus* can be compared to plants of *Helleborus niger* X *Helleborus* x *hybridus* 'COSEH 5600', disclosed in a U.S. Plant Patent application filed concurrently. Plants of the new *Helleborus* differ primarily from plants of 'COSEH 5600' in flower color as plants of the new *Helleborus* have white-colored flowers whereas plants of 'COSEH 5600' have yellow green, white and purple-colored flowers.

Plants of the new *Helleborus* can be compared to plants of *Helleborus niger* X *Helleborus* x *hybridus* 'COSEH 5700', disclosed in a U.S. Plant Patent application filed concurrently. Plants of the new *Helleborus* differ primarily from plants of 'COSEH 5700' in flower color as plants of the new *Helleborus* have white-colored flowers whereas plants of 'COSEH 5700' have red purple-colored flowers.

Plants of the new *Helleborus* can be compared to plants of *Helleborus niger* X *Helleborus* x *hybridus* 'COSEH 6900', disclosed in a U.S. Plant Patent application filed concurrently. Plants of the new *Helleborus* differ primarily from plants of 'COSEH 6900' in flower color as plants of the new *Helleborus* have white-colored flowers whereas plants of 'COSEH 6900' have light yellow green-colored flowers. In addition, plants of the new *Helleborus* are more vigorous than plants of 'COSEH 6900'.

Plants of the new *Helleborus* can be compared to plants of *Helleborus niger* X *Helleborus* x *hybridus* 'COSEH 7100', disclosed in a U.S. Plant Patent application filed concurrently. Plants of the new *Helleborus* differ primarily from plants of 'COSEH 7100' in flower color as plants of the new *Helleborus* have white-colored flowers whereas plants of 'COSEH 7100' have red purple-colored flowers.

Plants of the new *Helleborus* can be compared to plants of *Helleborus niger* X *Helleborus* x *hybridus* 'COSEH 7500', disclosed in a U.S. Plant Patent application filed concurrently. Plants of the new *Helleborus* differ primarily from plants of 'COSEH 7500' in flower color as plants of the new *Helleborus* have white-colored flowers whereas plants of 'COSEH 7500' have white to light yellow green-colored flowers. In addition, plants of the new *Helleborus* are more vigorous than plants of 'COSEH 7500'.

Plants of the new *Helleborus* can also be compared to plants of *Helleborus niger* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Leaves of plants of the new *Helleborus* are lighter green in color than leaves of plants of 'LEM 100'.
2. Flowers of plants of the new *Helleborus* are white in color whereas flowers of plants of 'LEM 100' are red purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 5900' grown in a container.

Figure 2:
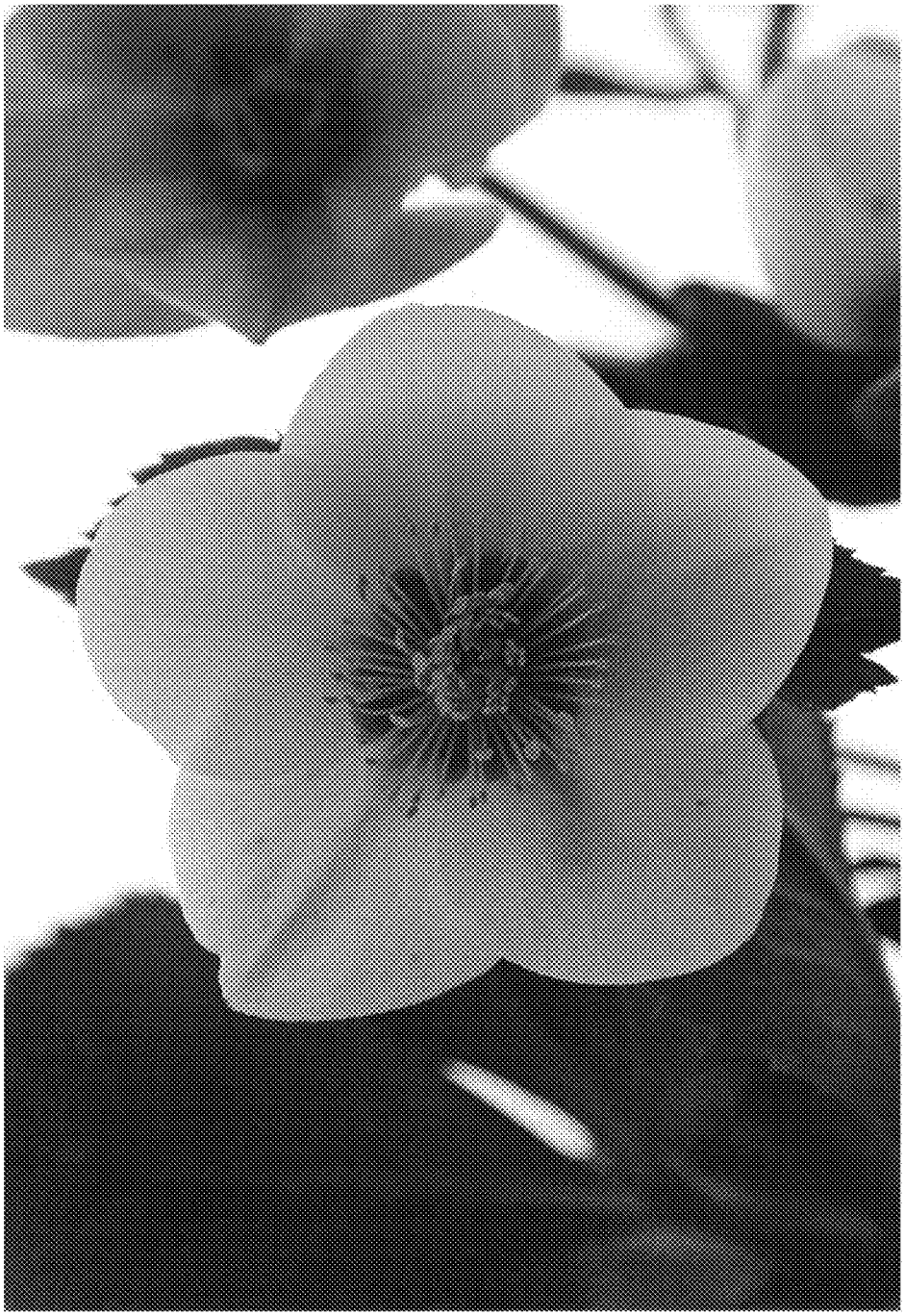

The photograph on the second sheet (FIG. 2 of 2) is a close-up view of typical flowers and leaves of 'COSEH 5900'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 5900'.

Parentage:

*Female, or seed, parent.*—Unnamed selection of *Helleborus niger*, not patented.

*Male, or pollen, parent.*—Unnamed selection of *Helleborus* x *hybridus*, not patented.

Propagation:

*Type.*—In vitro axillary meristem culture.

*Time to initiate roots, winter.*—About 55 days at temperatures about 12° C.

*Time to produce a rooted young plant, winter.*—About 170 days at temperatures ranging from 4° C. to 15° C.

*Root description.*—Thick to thin, fleshy; typically white to brown in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright and mounding plant habit with flowers held within and above the foliar plane; plant shape, roughly flattened globular; vigorous growth habit and moderate to rapid growth rate.

*Plant height, soil level to top of foliar plane.*—About 37 cm.

*Plant height, soil level to top of flowers.*—About 40.8 cm.

*Plant diameter (area of spread).*—About 45.7 cm.

Leaf description:

*Arrangement.*—Leaves arranged in a basal rosette; leaves palmately compound with typically seven leaflets per leaf.

*Leaf length.*—About 18 cm.

*Leaf width.*—About 21.1 cm.

*Leaflet length.*—About 9.3 cm.

*Leaflet width.*—About 6.5 cm.

*Leaf shape.*—Palmate; reniform in outline.

*Leaflet shape.*—Obovate to broadly obovate.

*Leaflet apex*.—Acute to broadly acute.

*Leaflet base*.—Attenuate.

*Leaflet margin*.—Serrate; slightly undulate to non-undulate.

*Leaflet texture and luster, upper surface*.—Smooth, glabrous; leathery; slightly to moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to NN137A; midvein distally, close to 183B. Developing leaflets, lower surface: Close to between 138A and 147B. Fully developed leaflets, upper surface: Darker than 147A; venation, close to 144B. Fully developed leaflets, lower surface: Close to 147B; venation, close to 145A to 145B.

*Petioles*.—Length: About 17.1 cm. Diameter: About 8 mm to 10 mm. Strength: Strong. Texture and luster, upper and lower surfaces: Smooth, glabrous; slightly to moderately glossy. Color, upper and lower surfaces: Close to 145A covered slightly to heavily with fine dots, close to 187A to 187D.

Flower description:

*Flower shape and habit*.—Single rotate flowers; flowers slightly cupped; arranged solitary or in clusters with about four flowers each; freely flowering habit with about 22 flowers developing per plant; flowers face mostly outwardly to slightly nodding or slightly upright.

*Fragrance*.—None detected.

*Natural flowering season*.—Plants begin flowering about ten months after planting; plants flower from the late autumn into the winter in Germany.

*Flower longevity on the plant*.—About three to four months; sepals persistent, other flower parts are not persistent.

*Flower buds*.—Length: About 1.8 cm. Diameter: About 1.1 cm. Shape: Ovate. Texture and luster: Smooth, glabrous; matte. Color: Close to between 145D and 157B; proximally, close to 145C.

*Inflorescence height*.—About 8.7 cm.

*Inflorescence diameter*.—About 16.2 cm.

*Flower diameter*.—About 8.3 cm by 8.3 cm.

*Flower depth* (*height*).—About 3 cm.

*Petals*.—All petals are transformed into nectaries.

*Sepals*.—Quantity and arrangement: About five, arranged in a single whorl. Length: About 4.7 cm. Width: About 4.2 cm. Shape: Broadly ovate, slightly concave. Apex: Obtuse. Base: Truncate to rounded. Margin: Entire; not undulate. Texture and luster, upper surface: Smooth, glabrous; matte. Texture and luster, lower surface: Smooth, glabrous; slightly glossy. Color: When opening, upper and lower surfaces: Close to NN155A and proximally, close to 145B; venation, similar to lamina color. Fully opened, upper surface: Close to NN155B and proximally, close to 145A; venation, similar to lamina color; with development, close to 145B and proximally, close to 145A. Fully opened, lower surface: Close to 155C, towards the margins and apex, close to NN155B and proximally, close to 145A to 145B; venation, similar to lamina color; with development, close to 145B and proximally, close to 145A.

*Flower bracts*.—Quantity per flower: Typically one or two. Length: About 5.3 cm. Width: About 3.4 cm. Shape: Ovate to broadly ovate. Apex: Acute. Base: Truncate. Margin: Serrate; slightly undulate to non-undulate. Color, upper surface: Close to between NN137A and 147A; venation, similar to lamina. Color, lower surface: Close to 147B; venation, similar to lamina.

*Peduncles*.—Length: About 30 cm. Diameter: About 6 mm to 7 mm. Aspect: About 10° from vertical. Strength: Strong. Texture and luster: Smooth, glabrous; moderately glossy. Color: Close to 144B; moderately to heavily covered with fine dots, close to between 183B and 187C.

*Pedicels*.—Length: About 4.4 cm. Diameter: About 3.5 mm to 4 mm. Aspect: About 10° from peduncle axis. Strength: Moderately strong. Texture and luster: Smooth, glabrous; moderately glossy. Color: Close to 144B moderately to heavily covered with fine dots, close to 183D.

*Reproductive organs*.—Stamens: Quantity per flower: About 100. Filament length: About 1.8 cm. Filament color: Close to NN155B. Anther shape: Double and broadly reniform; basifixed. Anther size: About 2 mm by 2 mm. Anther color: Close to 150C. Pollen amount: Moderate. Pollen color: Close to 4D. Pistils: Quantity per flower: About six to twelve. Pistil length: About 9 mm. Stigma diameter: About 0.3 mm. Stigma shape: Club-shaped. Stigma color: Close to 150D. Style length: About 8 mm. Style color: Close to 181C. Ovary color: Close to 145C. Nectaries (transformed petals): Quantity per flower: About twelve. Length: About 1.3 cm. Diameter: About 5 mm. Shape: Tubular, flattened. Texture and luster, inner and outer surfaces: Smooth, glabrous; slightly glossy. Color, immature, inner and outer surfaces: Close to 144A, distally, close to N144B and proximally, close to 146C. Color, mature, inner and outer surfaces: Close to 144A, distally, close to N144A to N144B and proximally, close to 146C; with development, close to 144A, distally, close to N144A and proximally, close to 146C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5900' as illustrated and described.

* * * * *